(12) United States Patent
Finlay et al.

(10) Patent No.: US 9,032,951 B2
(45) Date of Patent: May 19, 2015

(54) AEROSOL DELIVERY DEVICE

(75) Inventors: Bryan Finlay, London (CA); Michael Nuttall, London (CA); Brandon Coultes, Ilderton (CA); Mark Nagel, Mt. Brydges (CA); Mark Pickard, London (CA)

(73) Assignee: Trudell Medical International, London, Ontario (CA)

( * ) Notice: Subject to any disclaimer, the term of this patent is extended or adjusted under 35 U.S.C. 154(b) by 861 days.

(21) Appl. No.: 13/216,759

(22) Filed: Aug. 24, 2011

(65) Prior Publication Data

US 2012/0048264 A1    Mar. 1, 2012

Related U.S. Application Data

(60) Provisional application No. 61/376,644, filed on Aug. 24, 2010.

(51) Int. Cl.
*A61M 11/00* (2006.01)
*A61M 15/00* (2006.01)
(Continued)

(52) U.S. Cl.
CPC ............. *A61M 13/003* (2013.01); *A61M 11/06* (2013.01); *A61M 16/0463* (2013.01); *A61M 16/0816* (2013.01); *A61M 16/16* (2013.01); *A61M 2202/0225* (2013.01); *A61M 16/1095* (2014.02)

(58) Field of Classification Search
CPC ............ A61M 11/06; A61M 13/0003; A61M 16/0463; A61M 16/0816; A61M 16/1095; A61M 16/16; A61M 2202/0225
USPC ............. 128/203.12, 203.15, 203.19, 204.14, 128/207.14–207.16, 200.11–200.14, 128/200.18–200.22, 200.24; 239/427, 239/429–431; 600/153–159; 604/19, 604/23–26, 43, 45, 93.01, 131, 140, 147, 604/500, 514
See application file for complete search history.

(56) References Cited

U.S. PATENT DOCUMENTS

| | | |
|---|---|---|
| 3,864,326 A | 2/1975 | Babington |
| 4,537,188 A | 8/1985 | Phuc |

(Continued)

FOREIGN PATENT DOCUMENTS

| | | |
|---|---|---|
| EP | 0 692 273 A1 | 1/1996 |
| EP | 0 630 272 B1 | 4/2000 |

(Continued)

OTHER PUBLICATIONS

International Preliminary Report on Patentability issued in international application No. PCT/IB2011/001936, dated Feb. 26, 2013 (6 pages).

(Continued)

*Primary Examiner* — Tan-Uyen (Jackie) T Ho
*Assistant Examiner* — Mark K Han
(74) *Attorney, Agent, or Firm* — Brinks Gilson & Lione

(57) ABSTRACT

An aerosol delivery system is disclosed that is a single-use (disposable) continuous nebulizer system designed for use with mechanically ventilated patients to aerosolize medications for inhalation with a general purpose nebulizer, or for connection with devices usable in endoscopic procedures. The system separates the liquid reservoir from the nebulization process taking place either at the adapter hub, where it fits into an endotracheal tube (ETT), or a gas humidifier, where the aerosol may treat a gas used in an endoscopic procedure, with a multi-lumen tube configured to nebulize liquid and air at its distal end. The refillable liquid reservoir is mounted away from the immediate treatment zone, avoiding orientation issues associated with other types of nebulizers having a self-contained reservoir. The system can produce aerosols having a wide range of droplet sizes, depending upon central lumen diameter, with values of MMAD that range from 4 to 30 μm.

16 Claims, 8 Drawing Sheets

(51) Int. Cl.
| | |
|---|---|
| *A61M 16/00* | (2006.01) |
| *A61M 37/00* | (2006.01) |
| *A61M 13/00* | (2006.01) |
| *A61M 16/04* | (2006.01) |
| *A61M 16/08* | (2006.01) |
| *A61M 16/10* | (2006.01) |
| *A61M 11/06* | (2006.01) |
| *A61M 16/16* | (2006.01) |

(56) References Cited

U.S. PATENT DOCUMENTS

| | | |
|---|---|---|
| 4,986,269 A | 1/1991 | Hakkinen |
| 5,031,613 A | 7/1991 | Smith et al. |
| 5,186,166 A | 2/1993 | Riggs et al. |
| 5,277,175 A | 1/1994 | Riggs et al. |
| 5,313,939 A | 5/1994 | Gonzalez |
| 5,355,872 A | 10/1994 | Riggs et al. |
| 5,438,982 A | 8/1995 | MacIntyre |
| 5,474,059 A | 12/1995 | Cooper |
| 5,483,953 A | 1/1996 | Cooper |
| 5,522,385 A * | 6/1996 | Lloyd et al. ............. 128/203.26 |
| 5,579,758 A | 12/1996 | Century |
| 5,584,285 A | 12/1996 | Salter et al. |
| 5,642,730 A | 7/1997 | Baran |
| 5,884,846 A | 3/1999 | Tan |
| 5,906,198 A | 5/1999 | Flickinger |
| 5,964,223 A | 10/1999 | Baran |
| 6,079,413 A | 6/2000 | Baran |
| 6,116,516 A | 9/2000 | Gañán-Calvo |
| 6,119,953 A | 9/2000 | Gañán-Calvo et al. |
| 6,234,402 B1 | 5/2001 | Gañán-Calvo |
| 6,340,023 B2 | 1/2002 | Elkins |
| 6,357,670 B2 | 3/2002 | Gañán-Calvo |
| 6,405,936 B1 | 6/2002 | Gañán-Calvo |
| 6,526,976 B1 * | 3/2003 | Baran ....................... 128/207.14 |
| 6,536,423 B2 | 3/2003 | Conway |
| 6,595,202 B2 | 7/2003 | Gañán-Calvo |
| 6,729,334 B1 | 5/2004 | Baran |
| 6,766,801 B1 | 7/2004 | Wright |
| 6,792,940 B2 | 9/2004 | Gañán-Calvo |
| 7,059,319 B2 | 6/2006 | Ganan-Calvo |
| 7,059,321 B2 | 6/2006 | Ganan-Calvo |
| 7,267,121 B2 | 9/2007 | Ivri |
| 7,290,541 B2 | 11/2007 | Ivri et al. |
| 7,334,580 B2 | 2/2008 | Smaldone et al. |
| 7,448,376 B2 | 11/2008 | Lepel |
| 7,469,700 B2 | 12/2008 | Baran |
| 7,472,705 B2 | 1/2009 | Baran |
| 7,600,511 B2 * | 10/2009 | Power et al. ............. 128/200.24 |
| 7,607,436 B2 | 10/2009 | Smaldone et al. |
| 7,712,466 B2 | 5/2010 | Addington et al. |
| 7,748,377 B2 | 7/2010 | Smith et al. |
| 8,051,854 B2 | 11/2011 | Faram |
| 8,322,334 B2 | 12/2012 | Lee et al. |
| 2002/0072700 A1 | 6/2002 | Mantell et al. |
| 2007/0049841 A1 | 3/2007 | Lepel |
| 2007/0137648 A1 | 6/2007 | Addington et al. |
| 2008/0066741 A1 | 3/2008 | LeMahieu et al. |
| 2008/0230053 A1 | 9/2008 | Kraft et al. |
| 2008/0283051 A1 | 11/2008 | Faram |
| 2009/0308384 A1 | 12/2009 | Power et al. |
| 2010/0204602 A1 | 8/2010 | Addington et al. |
| 2011/0105936 A1 | 5/2011 | Addington et al. |
| 2012/0167878 A1 | 7/2012 | Belson et al. |

FOREIGN PATENT DOCUMENTS

| | | |
|---|---|---|
| EP | 0 687 478 B1 | 9/2001 |
| EP | 0 692 273 B1 | 4/2004 |
| WO | 93/17744 A1 | 9/1993 |
| WO | WO 2004/011070 A1 | 2/2004 |
| WO | 2004/071368 A2 | 8/2004 |
| WO | 2004/071368 A3 | 8/2004 |
| WO | 2008/094219 A2 | 8/2008 |
| WO | 2009/117422 A2 | 9/2009 |
| WO | 2009/117422 A3 | 9/2009 |
| WO | 2010/008424 A2 | 1/2010 |

OTHER PUBLICATIONS

European Directorate for the Quality of Medicines (EDQM), Preparations for Nebulisation: Characterisation (2.9.44), *Pharm. Europa*, 2006,18(2):280-282.

Fink, James B., New Technology Offers New Opportunities: Continuous Bronchodilator Therapy During Mechanical Ventilation, *Respiratory Therapy*, Aug.-Sep. 2007, 2(4):29-32.

Finlay, J. B. et al., Delivery of Medication as Large Particles at the Carina of an In Vitro Lung Model is Effective Using a Nebulizing Catheter, Drug Delivery to the Lungs-16, Edinburgh, UK, Dec. 2005, pp. 34-37.

Günther, A. et al., Tidal Volume in Mechanical Ventilation: The Importance of Considering Predicted Body Weight, *Am. J. Respir. Crit. Care Med.*, 2008,178:315-316.

Hess, Dean R., Nebulizers: Principles and Performance, *Respir. Care*, Jun. 2000, 45(6):609-622.

Instruction manual for the Aeroneb® Solo System Micropump Nebulizer, Aerogen Ltd, Galway, Ireland, 2009 available at: http://aerogen.com/uploads/File/TrainingMaterial/Solo/Aeroneb%20Solo%20DFU%20%20Rev%20F%20-%20EN.pdf.

Kesser, K. C., et al., New Aerosol Delivery Devices for Cystic Fibrosis, *Respiratory Care*, Jun. 2009, 54(6):754-768.

McPeck Michael, et al., Aerosol Delivery During Continuous Nebulization, *Chest*. 1997, (111):1200-1205.

Mitchell, J. P., et al., Relative Precision of Inhaler Aerodynamic Particle Size Distribution (APSD) Metrics by Full Resolution and Abbreviated Andersen Cascade Impactors (ACIs): Part 1, *AAPS PharmSciTech*, 2010, 11(2):843-851.

Mitchell, J. P., et al., Relative Precision of Inhaler Aerodynamic Particle Size Distribution (APSD) Metrics by Full Resolution and Abbreviated Andersen Cascade Impactors (ACIs): Part 2—Investigation of Bias in Extra-Fine Mass Fraction with AIM-HRT Impactor, *AAPS PharmSciTech*, 2010, 4 pages.

Usmani, O. S., et al., Effects of bronchodilator particle size in asthmatic patients using monodisperse aerosols, *J Appl Physiol*, 2003, 95:2106-2112.

Usmani, O. S., et al., Regional Lung Deposition and Bronchodilator Response as a Function of $\beta_2$-Agonist Particle Size, *Am. J. Respir. Crit. Care Med.*, vol. 172, 2005, 172:1497-1504.

European Search Report issued in European application No. EP11871358.5, dated Mar. 13, 2015.

* cited by examiner

AEROSOL DELIVERY DEVICE

CROSS-REFERENCE TO RELATED APPLICATIONS

This application claims the benefit of U.S. Provisional Application No. 61/376,644, filed Aug. 24, 2010, the entirety of which is hereby incorporated herein by reference.

TECHNICAL FIELD

This disclosure relates to an aerosol delivery device for nebulizing a liquid for administration or delivery to a predetermined location in the interior or exterior of a human or animal. More particularly, this disclosure relates to an aerosol delivery device for use in ventilator applications to administer or deliver a liquid medicament or other liquid substance in aerosol form to a human's or animal's respiratory system, or for use in endoscopic applications to administer or deliver a liquid medicament or other liquid or substance in aerosol form.

BACKGROUND

Conventional jet nebulizers require a significant amount of air for their operation, typically 15 liters per minute (L/min). With a typical I:E ratio of 1:3 and 15 breaths per minute (BPM), such a nebulizer would generate 1,000 milliliters (mL) of aerosol during a typical 4-second period of inspiration expiration. The tidal volume of a healthy adult may be on the order of 700 mL and that of a pediatric patient will generally be far less. Consequently, the large air flows provided by conventional jet nebulizers, when introduced into a ventilator circuit, may cause the sensing mechanisms of the ventilator circuit to produce alarms and potentially shut down its operation.

Nebulizer systems, such as micro pump systems, do not require a supply of air flow for their operation. Thus, they may be used in neonatal and adult ventilator circuits without fear of conflicting with the ventilator circuit sensors. Although micro pump nebulizer systems address the potential air flow problems that may occur when used with ventilator circuits, the attachments for a micro pump nebulizer system that would be used with the ventilator circuit are generally heavy, especially for pediatric application. Furthermore, the micro pump nebulizer systems are generally required to be kept upright during use.

Another way in which nebulizing devices have been implemented to avoid conflicting with the sensing mechanisms of a ventilator is to utilize nebulizing systems for delivering target aerosol directly into the lungs such as a nebulizing catheter synchronized with a patient's breathing to aid in the delivery of expensive or potential toxic drugs, and also to reduce environment contamination with certain drugs. These types of nebulizing systems are typically driven by a control unit to make sure the pressures of producing the aerosol do not conflict with the ventilator circuit activity. Specifically, some nebulizing systems would use a separate control unit that synchronizes with the ventilation pressure and only produce aerosol during the initial stages of inhalation, for example the first 70 percent of inhalation. These nebulizing systems are generally designed for higher pressure gas supply operation, for example 100 pounds per square inch (p.s.i.) thereby requiring a separate compressor or gas cylinder in addition to the control unit that manages when the pressurized gas is applied to generated aerosol.

Accordingly, there is a need for an improved aerosol delivery system for use with ventilators that makes up for the above-noted issues.

BRIEF SUMMARY

In order to address the concerns of existing nebulizers and nebulizing systems that can be used with ventilator circuits, a ventilator aerosol delivery system is disclosed herein which may provide a lightweight portable system that can function without separate control units and use standard available sources of pressurized gas rather than higher pressure and/or adjustable pressure gas sources often used with nebulizing systems.

According to a first aspect an aerosol delivery system includes a vessel with a first end comprising a resealable fitting for connecting with a gas supply. The vessel also includes a body having a liquid reservoir and a gas passage independent of the liquid reservoir, where the liquid reservoir and the gas passage are in communication with gas supply via the resealable fitting, and where the body is configured to be adjacent to the resealable fitting when the resealable fitting is attached to the gas supply. A second end of the vessel is connected with a length of multi-lumen tubing. The second end defines a liquid path from the liquid reservoir to a liquid lumen in the multi-lumen tubing and a gas path from the gas passage to at least one gas lumen in the multi-lumen tubing. The aerosol delivery system also includes a tube adapter, such as an endotracheal tube adapter, having an inlet port connected to an end of the multi-lumen tubing, and tube opening sized to connect with a tube such as an endotracheal tube, where outlets for the gas and liquid lumens at the end of the multi-lumen tubing are arranged such that gas issuing from the at least one gas lumen and liquid issuing from the liquid lumen continuously form an aerosol inside the tube adapter. Gas received at the resealable fitting provides gas for both the at least one gas lumen and provides a pressure to any liquid in the liquid reservoir. In an alternative embodiment, the aerosol delivery system may be configured for use in endoscopic procedures rather than respiratory applications. For example, rather than being connected to an endotracheal tube adapter, the multi-lumen tubing may be connected to a tubing, such as a wye-tube, or to a device connected to the tubing, such as a gas warmer or gas warmer/humidifier device. The tubing carries a gas and in one embodiment the gas is $CO_2$ and it is used in an endoscopic procedure, such as a laparoscopic procedure, for insufflating a body cavity and the multi-lumen tubing is used to administer, for example, a liquid such as $H_2O$ in aerosol form, to humidify or to further humidify the $CO_2$ gas used to insufflate the body cavity.

The body of the vessel may have a one-way filling port positioned over the liquid reservoir of the vessel to permit refilling of the reservoir. The one-way filling port may be positioned at an angle from a vertical orientation of the body. The resealable fitting on the vessel may be configured to rigidly attach the vessel to an outlet of the gas supply, when the resealable fitting is tightened onto the outlet, so that orientation of the reservoir is maintained and the reservoir is kept away from the patient to avoid potential clutter at the location of treatment. The continuously formed aerosol produced in the endotracheal tube adapter at the end of the multi-lumen tubing may produce particle sizes in a range of 10-14 µm MMAD when gas at a pressure of 50 pounds per square inch (psi) is received at the resealable fitting.

BRIEF DESCRIPTION OF THE DRAWINGS

For the purpose of facilitating an understanding of the subject matter sought to be protected, there is illustrated in the accompanying drawings an embodiment thereof, from an inspection of which, when considered in connection with the following description, the subject matter sought to be protected, its construction and operation, and many of its advantages should be readily understood and appreciated.

DETAILED DESCRIPTION

Figure 1:
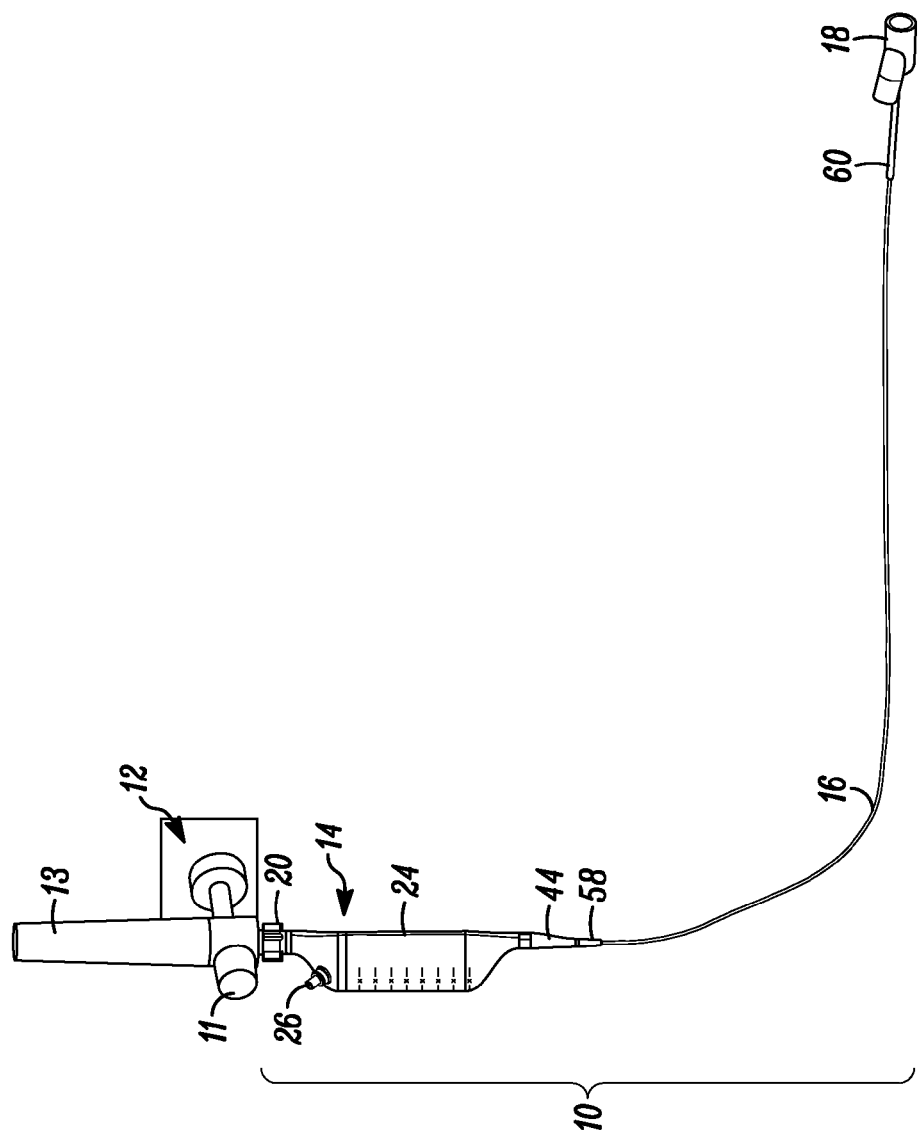
FIG. 1 illustrates an implementation of a ventilator aerosol delivery system connected to a healthcare facility wall-outlet.

Referring to FIG. 1, an aerosol delivery system 10 is shown connected to a typical wall outlet connection for pressurized gas 12. The typical wall outlet connection point is a flow meter 13 having a gas flow control knob 11, although the aerosol delivery system 10 may also be connected directly to the wall outlet. The aerosol delivery system 10 includes a liquid vessel 14, multi-lumen tubing 16 carrying the gas and a liquid from the liquid vessel, and a connection such as an endotracheal tube adapter 18 into which an aerosol generated at the end of the multi-lumen tubing 16 is directed. The wall outlet 12 may be a typical healthcare facility wall outlet that provides a supply of compressed medical air and is in a fixed position on the wall of the healthcare facility. The wall outlet 12 may have a suitable DISS (diameter index safety system) fitting connection to the supply of medical compressed air at the healthcare facility. A nominal pressure of medical air supplied by the wall outlet connection may be 50 p.s.i. The liquid vessel 14 may directly connect to the wall outlet 12 with a threaded connector 20 that is movably attached to the liquid vessel 14.

Figure 2:
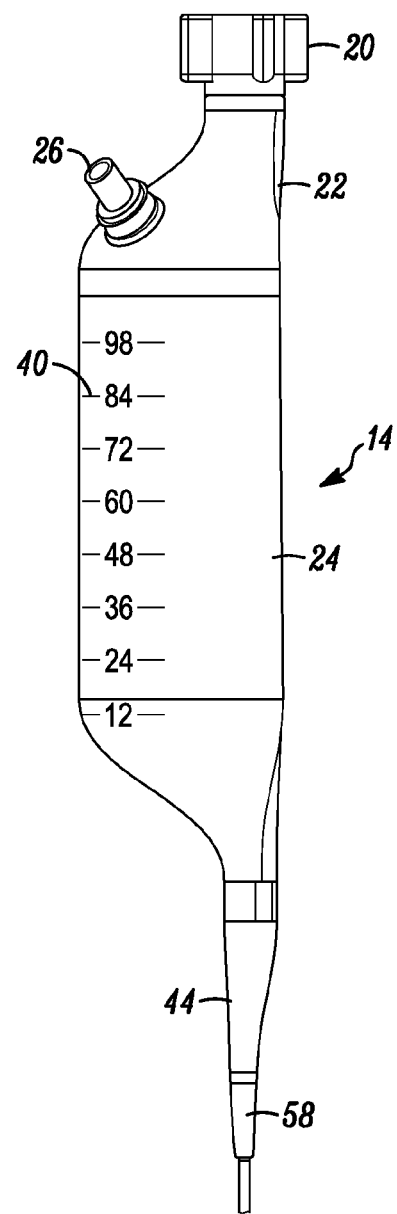
FIG. 2 is an enlarged view of the liquid vessel of the ventilator aerosol delivery system of FIG. 1.
Figure 3:
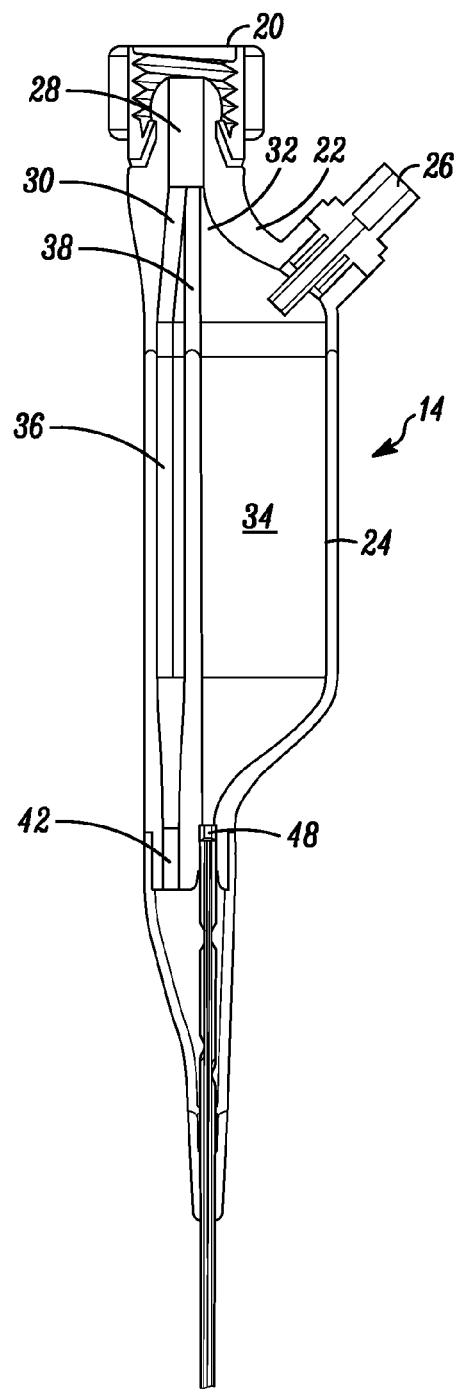
FIG. 3 is a cross-sectional view of the liquid vessel of FIG. 3.

As shown in FIGS. 2 and 3, the connector 20 is rotatably attached to an upper portion of the liquid vessel 14 and may be a 9/16-18 UNF female connector with a 10 mm diameter nipple. The connection is designed to directly interface with the standard 9/16-18 UNF conical male fitting employed on medical gas flow meters of wall outlets such as wall outlet 12. The liquid vessel 14 includes an inlet module 22 and a main body 24. The connector 20 is formed in the inlet module 22. A one-way filling port 26 on the inlet module 22 provides a port for allowing a liquid medicament to be added to the liquid vessel 14. The one-way filling port 26 may include a Luer fitting to accommodate filling from a standard syringe in accordance with the ISO 594-1 standard. Also, to allow easier access to the filling port and avoid interference from the wall outlet 12 or other mounted paraphernalia on a healthcare facility wall, the one-way filling port 26 is formed at an angle from the wall such that when the liquid vessel is attached to the wall outlet, the liquid outlet and wall form a non-zero angle, such as a 45 degree angle.

As best shown in FIG. 3, the connector 20 rotatably fits on the end of an air channel 28 formed in the inlet body 22. The air channel 28 splits inside the inlet body 22 into a bypass channel 30 and a liquid reservoir channel 32. The main body 24 of the liquid vessel 14 includes a liquid reservoir region 34 and an air passage 36. The liquid reservoir 34 and air passage 36 are separated by a dividing wall 38 that begins where the bypass channel 30 and liquid reservoir channel 32 separate and continues on until the bottom of the liquid vessel 14 such that two separate chambers are formed. The walls of the main body 24 of the liquid vessel 14 surrounding the air passage 36 and liquid reservoir 34 may be completely transparent, or semi-opaque to permit easy view of any liquid levels in the liquid reservoir 34 or contaminants in either section. A group of liquid vessel graduation marks 40 may be positioned along the vertical length of the main body adjacent the liquid chamber. The liquid vessel graduation marks 40 may be arranged as appropriate for the particular capacity of the liquid reservoir 34 in the liquid vessel 14. Various capacities of the reservoir for medicament are contemplated, for example 12 milliliter (mL) or 96 mL versions of the liquid vessel may be desired. The smaller reservoir may be utilized intended for short term treatment, analogous to that given by a small volume jet nebulizer, while embodiments with the larger reservoir may be used to deliver medication over extended periods (continuous nebulization), as is currently provided by large volume jet nebulizers when used with a drip-bag option. Medication suitable for delivery includes, without limitation, salbutemol, budesonide and ipratropium bromide.

Referring again to FIG. 3, where the air channel 28 splits into a bypass channel 30 and liquid reservoir air channel 32, the liquid reservoir air channel 32 provides the top of the reservoir 34 with pressure directly from the wall outlet such that medicament receives enough pressure to force the liquid through to the bottom of the liquid reservoir 34 to the end of the multi-lumen tubing 16 at the bottom of the liquid reservoir 34. The distal end of the liquid reservoir 34 preferably tapers into a small outlet sized to receive the multi-lumen tubing 16.

At the bottom end of the liquid vessel 14, as noted above, multi-lumen tubing 16 is attached at the bottom of the liquid reservoir 34. Additionally, adjacent to the multi-lumen tubing is an opening of the air passage 36. The bottom of the liquid vessel 14, surrounding the air passage opening 42 and the connection with the multi-lumen tubing 16, defines a connection hub 44. The connection hub 44 may attach to the liquid vessel 14 at a friction fit joint 46 and may additionally or alternatively be bonded or adhered. The multi-lumen tubing 16 may form an adhesive bonded fit, or be joined with the liquid vessel using any of a number of bonding or welding techniques, with the opening at the bottom of the liquid reservoir 34. The reservoir 34 is sealed to the proximal end of the multi-lumen tube in this manner not only to provide an airtight connection and prevent leakage, but also to prevent switching the liquid vessel 14, or multi-lumen tubing 16 to another system 10, which could lead to contamination or performance issues. The reservoir 34 is replenished via a syringe connected via the luer-lock fitting of the one-way fill port 26

A liquid filter 48 is positioned at the junction of the reservoir 34 and the multi-lumen tubing 16 so as to remove any contaminants from liquid prior to entry into the multi-lumen tubing. The liquid filter 48 may be a stainless steel mesh or any of a number of other suitable liquid filters. In one embodiment, the stainless steel mesh of the liquid filter may be a steel mesh of approximately 15-25 micrometers (µm) pore size on the stainless steel carrier. The liquid filter 48 may be press fit into the bottom of the channel in the liquid reservoir.

Figure 4:
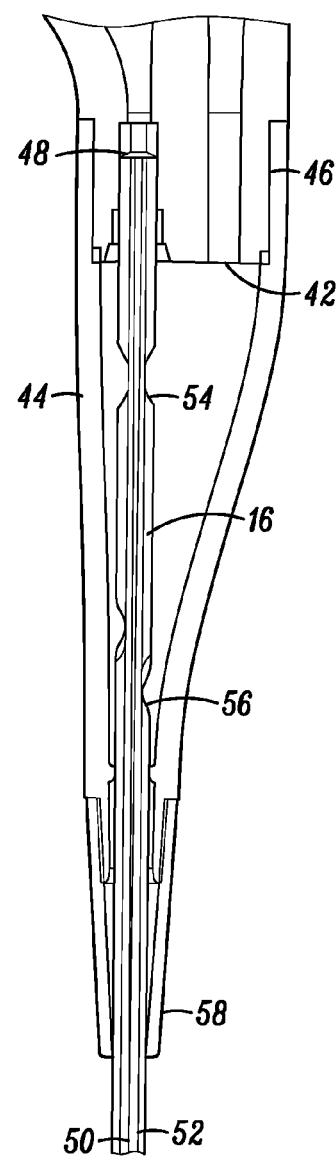
FIG. 4 is a bottom sectional view of the liquid vessel of FIG. 2.

FIG. 4 illustrates a cross-sectional view of the bottom of the liquid vessel 14 through a portion where the multi-lumen tubing 16 begins. The parallel air passage outlet 42 and opening in the liquid reservoir containing the multi-lumen tubing 16 are shown in greater detail. The multi-lumen tubing 16 includes multiple lumens with a central lumen 50 and one or more peripheral lumens 52. The multi-lumen tubing terminates in the endotracheal tube adapter 18 in a tapered portion with the lumens aligned to generate an aerosol as the air and liquid are ejected under pressure supplied by the wall-outlet 12. Various arrangements and positioning of tubing with multiple lumens are contemplated. Examples of various suitable multi-lumen tubing 16 may be found in U.S. Pat. No. 5,964,223, entitled Nebulizing Catheter System and Methods of Use and Manufacture, the entirety of which is incorporated herein by reference.

Figure 5:
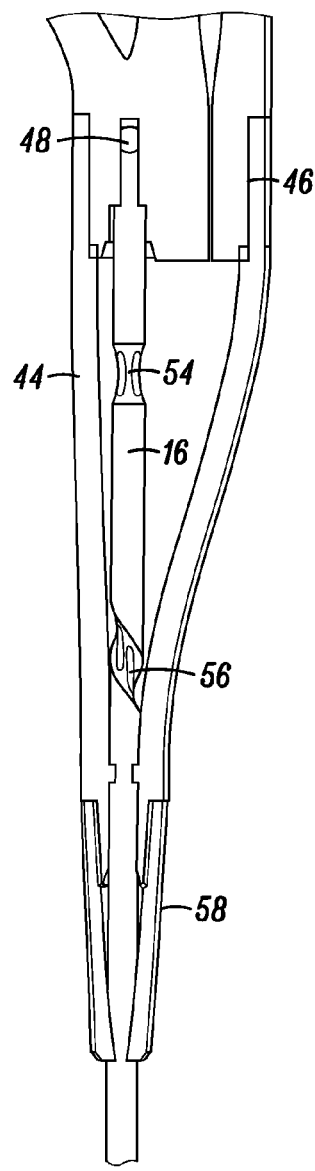
FIG. 5 is an enlarged cross-sectional view of the distal end of the liquid vessel illustrated in FIG. 3.
Figure 6:
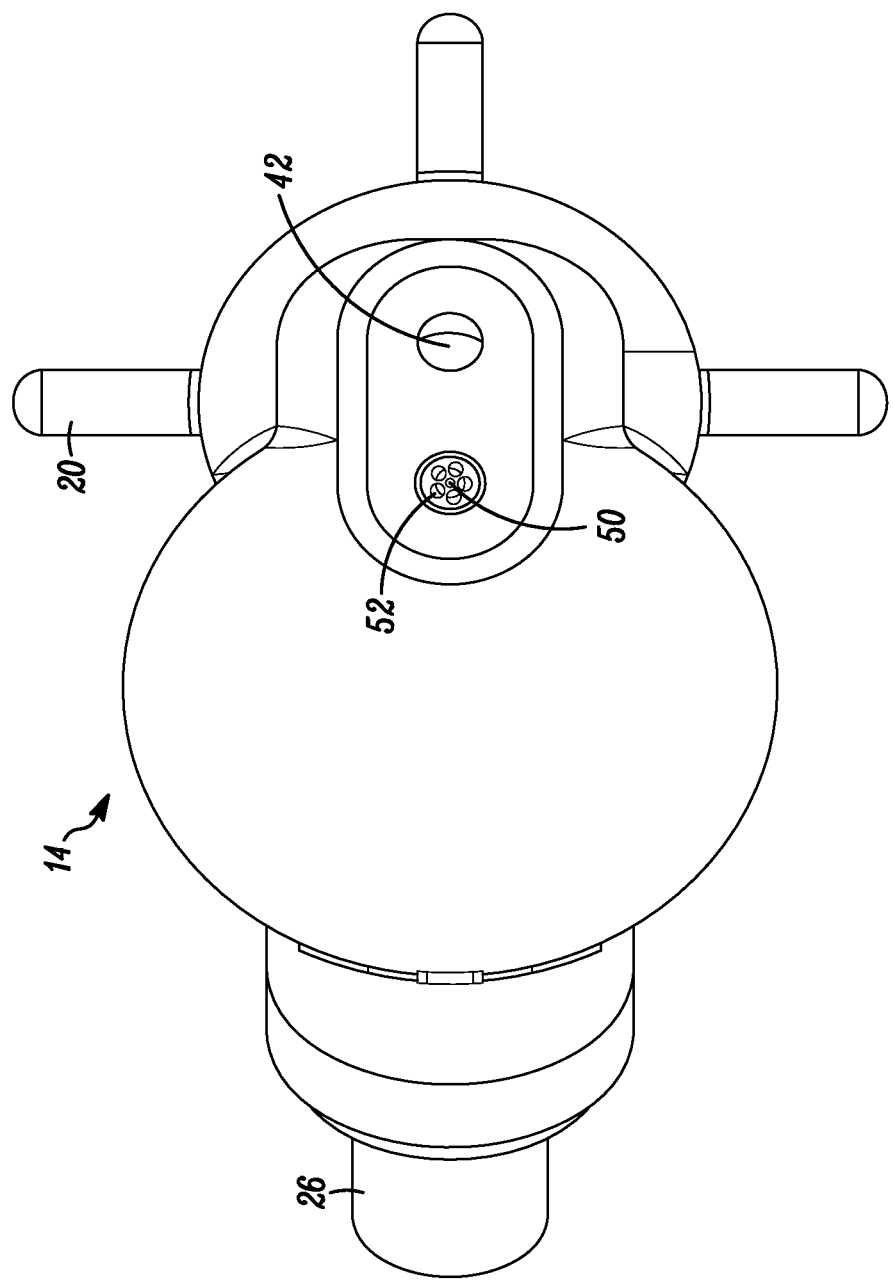
FIG. 6 is looking proximally at an enlarged partial cross-sectional view of the distal end of the liquid vessel illustrated in FIG. 3.

At the initial portion of the multi-lumen tubing 16 where liquid from the liquid reservoir 34 enters the multi-lumen tubing 16, all of the lumens 50-52 receive liquid. Referring to FIGS. 5-6, a break 54 in some of the lumens allows selective blocking of those lumens in the multi-lumen tubing 16 just below the connection of the multi-lumen tubing 16 to the liquid reservoir 34. This break 54 is used to preferably block one or more of the peripheral lumens 52 so that no liquid from the liquid reservoir 34 may pass further down the multi-lumen tubing 16 through the blocked lumens. The blockage of the lumens may be performed by a heat melting of the extruded multi-lumen tubing or applying a glue that blocks specific lumens in the multi-lumen tubing. In the five peripheral lumen 52 embodiment illustrated, all peripheral lumens may be blocked at the break 54 in one implementation.

Further down the multi-lumen tubing 16, away from the liquid vessel with respect to the break 54, are lumen openings 56 that provide an avenue to communicate air coming from the air outlet 42 of the air passage 36 to the lumens 52 that were blocked at the break 54. Air traveling through the connection hub 44 is directed into the openings 56 and thus to the distal end of the multi-lumen tubing 16. In other words, pressurized air from the wall outlet 12 which passes through the air passage 36 in air outlet 42 into the connection hub 44 is then projected into the open lumens at the opening 56. Medicament from the liquid reservoir 34 in the liquid vessel 14 continues in the multi-lumen tubing 16 in a central lumen 50 and/or any other lumens not blocked at the blocking portion 54.

The distal end of the connection hub 44 is sealed around the multi-lumen tubing 16, for example with an adhesive or glue, to prevent gas leakage. A strain relief member 58 is attached to the end of the connection hub 44. The strain relief member 58 may be a bendable tip having a length sufficient to provide a transition between the rigid connection hub 44 and the more flexible multi-lumen tubing 16. Also, as best shown in FIGS. 2 and 3, the connection hub 44 tapers and curves away from the side of the liquid vessel 14 intended to be oriented nearest a wall when the connector 20 is attached to the healthcare facility gas supply outlet 12. In this manner, the multi-lumen tubing 16 and strain relief tip 58 are spaced away from the wall, when the connector 20 is attached to the wall-mounted gas supply, and are less likely to interfere with other equipment, tubing or outlets that may be mounted on or near the same wall.

Figure 7:
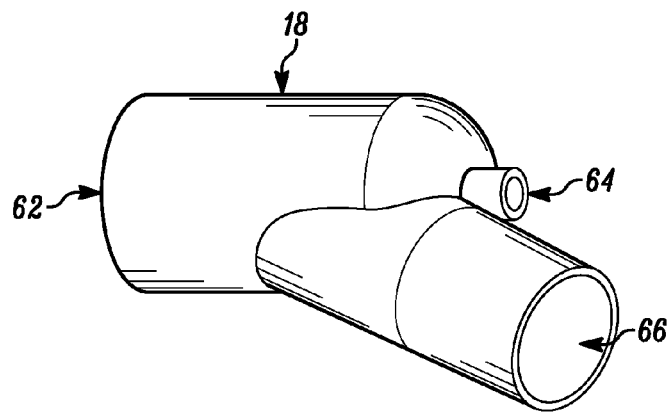
FIG. 7 illustrates an endotracheal tube adapter suitable for use in the system of FIG. 1.
Figure 8:
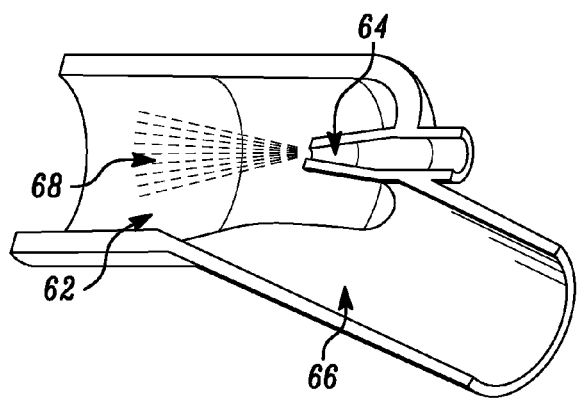
FIG. 8 is a cross-section of the adapter of FIG. 7 showing a location of aerosol mist that will be generated by the tip of multi-lumen tubing of the system of FIG. 1.

In operation, the multi-lumen tubing 16 leaving the strain relief region 58 contains the flow of air from the wall-mounted outlet 12 in the peripheral lumens 52 and liquid in the central lumen 50. The multi-lumen tubing 16 preferably extends from the liquid vessel 14 to an adapter such as the endotracheal tube adapter 18 over a distance of approximately 2 to 3 meters. The multi-lumen tubing 16 connects with the endotracheal tube (ETT) adapter 18 over a short strain relief sleeve 60 to provide strain relief at the point where the multi-lumen tubing and the endotracheal tube adapter meet. As shown in FIGS. 7-8, the ETT adapter 18 has an ET Tube connection end 62 for connecting to endotracheal tube, an insertion port 64 sized to receive the multi-lumen tubing 16 and strain relief sleeve 60, and a suction catheter connection port 66 for receiving a suction catheter. The ET Tube connection end may be a standard 15 mm diameter tapered connection in compliance with ISO standard 5356-1.

The tip of the multi-lumen tubing 16 is preferably tapered such that the tubing 16 extends into the insertion port 64 slightly more than the sleeve 60 and the air and liquid lumens 52, 50 are oriented to mix the air and liquid into a nebulized mist 68 into the ETT adapter 18 as shown in FIG. 8. In one implementation, the multi-lumen tubing 16 may be tubing having a nominal 2 mm outside diameter at its proximal end (i.e. adjacent the liquid vessel 14) and tapering to about 0.4 to 0.6 mm, but preferably about 0.5 mm, outside diameter over the portion that extends into the insertion port 64 of the ETT adapter 18. A desired range of particle sizes is 10-14 μm mass median aerodynamic diameter (MMAD) when air at a pressure of 50 pounds per square inch (psi) (345 kiloPascals (kPa)) is applied to the gas lumens 52 and to liquid in the reservoir 34 of the liquid vessel 14. The resultant air flow-rate may be on the order of 0.6 L/minute (600 mL/min) and the liquid flow-rate may be about 0.4 mL/minute.

The size of the multi-lumen tubing 16 and lumens 50, 52 may be selected to achieve desired particle size and flow rates for a given gas pressure. In one embodiment the multi-lumen tubing 16 may have one central lumen and several outside lumens, typically 4 to 6, with nominal diameters of 0.012 inches and 0.02 inches respectively at the proximal end. The multi-lumen tubing can be provided in various lengths, with one suitable length being about 3 meters as mentioned above. At the tip of the multi-lumen tubing inside the insertion port 64, the outer lumens 52 may be sized with a diameter 0.0032±0.00015" and the inner lumen (carrying the liquid under pressure provided from a portion of the gas supply of the wall outlet 12) may be size at a diameter of 0.0024±0.00005". The outer lumens may be arranged on a 0.0074±0.00006" pitch circle diameter. One can produce a different particle size distribution with the system by adjusting the lumen 50, 52 diameters while maintaining the same wall thickness between the lumens.

Preferably the multi-lumen tubing 16, liquid vessel 14, and filter element 48 will all be made of chemically-resistant materials suitable for working with the medications intended, including, without limitation, salbutemol, budesonide and ipratropium bromide. Generally these materials should satisfy USP class VI (ISO 10993-1). One generally good material for the multi-lumen tubing is a polyamide, such as Nylon-12. As noted above, the filter element 48 may be a stainless steel mesh of a stainless steel carrier. I an alternative embodiment, the filter may be a monofilament polyamide, such as Nylon 6-6 (Sefar Medifab). Other materials are contemplated. The endotracheal tube adapter 18 and the components of the liquid vessel 14 generally should be made of a durable, biocompatible material with a reasonable degree of impact resistance. As noted above, the main body 24 of the liquid vessel 14 may be clear or have a clear section to provide a room for visual assessment of the amount of liquid within reservoir 34. One suitable material for these components is Zylar (a styrene methyl methacrylate acrylic copolymer).

The connector 20 at the side of the of the inlet module 22 of the liquid vessel 14 may be made from ABS or other material with a suitable strength. The one-way fill port 26 may be made from a combination of materials, such as ABS and silicone rubber. The strain reliefs tip 58 and sleeve 60 may be made from a flexible material that can be readily bonded to the associated parts. The strain relief tip and sleeve 58, 60 are preferably not in contact with the medical gas or liquid medication and a suitable material for these elements is PVC or polyurethane. Also, the bonding of adjacent parts in the system 10 should satisfy biocompatibility requirements for any of the airways or liquid pathways. Examples of suitable bonding techniques include ultrasonic welding or UV-curing adhesives. Although reusable versions are contemplated, the aerosol delivery system 10 is preferably a single-use, disposable item.

Although numerous configurations are contemplated, in one implementation, the following dimensions may be used. The liquid vessel 14 may have an inlet module 22 that fits within a 24×13 mm cross-section and is approximately 34 mm high for a 10 mL reservoir 34, or can fit in a 48×42 mm cross-section and is approximately 42 mm high for a 100 mL reservoir 34. The main body of a 10 mL version and a 100 ml version may be 83 mm high and 126 mm high, respectively, and fit within the same respective cross-sections identified above. The one-way filling port 26 may be 1.75" long with a 0.25" outside diameter and a 0.375" diameter outer flange. The connection hub 44 may fit within a 0.3"×0.5" cross-sectional area and is nominally 1.4" to 1.8" in length. The strain relief tip 58 is nominally 25 mm in length with inside dimensions to fit the tip of the Connection Hub 44 and the nominal 2-mm-diameter proximal end of the multi-lumen tubing 16. In the liquid vessel 14, the air passage 36 within the main body 24 is nominally 4×8 mm in cross-section. For the portion of the air inlet 28 that branches into the liquid reservoir air channel 32, the nominal ⅛" diameter inlet 28 is divided into two channels that provide inlets to the air passage 36 and the inlet to the liquid reservoir 34. The inlet of the liquid reservoir air channel 32 to the liquid reservoir 34 is on the order of 1.5 $mm^2$. Also, the inside and outside diameters of the strain relief sleeve 60 are nominally 1/16" and ⅛" respectively, with a length sufficient to provide a snug fit at its proximal contact with the multi-lumen tubing 16. This length may be typically 30 cm.

In operation, the system 10 provides for continuous aerosolization of a medication that has been provided in a suitable concentration to permit continuous delivery until the reservoir 34 of the liquid vessel 14 is empty. A brief description of system set-up and operation is described below. A packaged system 10 may be opened by a healthcare provider and inspected for any signs of damage or broken seals on the package. After removal from the packaging, the healthcare provider connects the connector 20, such as a 9/16-18 UNF female connector, to the supply of medical gas from a wall-mounted flow-meter 12. The multi-lumen tubing 16 is then uncoiled and the endotracheal tube adapter 18 may be connected the endotracheal tube, a suction catheter (if required) and ventilator circuit. Clips or other suitable restraints may be applied along the length of the multi-lumen tubing 16, as necessary, to ensure that the tubing 16 does not accidentally experience excessive forces while in use.

Once the system 10 is secured and assembled, the healthcare provider may provide medicament to the reservoir 34 or the system 10 may be prefilled and packaged with the desired medication. In one implementation, it is contemplated that the healthcare provider could insert a pre-filled syringe into the one-way filling port 26 and twist the tapered Luer connection of the port to ensure a firm contact. If necessary, the healthcare provider may repeat this filling process until the desired volume of liquid medication is in the reservoir 34. The graduations 40 on the main body 24 of the liquid vessel 14 may be used to confirm that the desired amount of medication has been introduced into the liquid vessel 14. The flow through the flow regulator of the healthcare facility wall outlet 12 may now be adjusted to maximum, since the dimensions of the outer lumens of the multi-lumen tubing will govern the flow-rate of air exiting the tip of the multi-lumen tubing 16 in the ETT adapter 18. At this stage, the aerosol 68 generated at the tip of the multi-lumen tubing 16 will begin to be delivered into an ET Tube (not shown) connected to the ETT adapter 18. If the liquid vessel 14 requires re-filling during the treatment of the patient, the fresh liquid medication can be introduced using a syringe while the circuit is still pressurized at 50 psi. The pressure required on the plunger of the syringe when filling a pressurized circuit will be greater than when the circuit was not pressurized, but should still be achievable with a force applied by the thumb and fingers of one hand. When the treatment is complete, the flow meter to may be adjusted to zero flow, the 9/16-18 UNF female connector removed from the flow meter, and the system 10 disconnected from the ET Tube, suction catheter (if present), and the ventilator circuit. The system 10 should then be completely disposed of as required by the procedures of the healthcare facility.

An additional embodiment directed to an apparatus for use in an endoscopic procedure is illustrated in FIG. 9. Rather than using the system 10 for a respiratory application, the system may be modified for endoscopic applications by removing the ventilator adaptor 18 of FIGS. 7-8 (see also FIG. 1) and instead inserting the multi-lumen tubing 16 into a port of a gas warmer and/or humidifier 100 such as shown. The multi-lumen tubing may be a nebulizing catheter that is designed to pierce a membrane on the port of the gas warmer and/or humidifier and introduce a nebulized substance into the gas warmer, or it may terminate in any of a number of known connectors designed to cooperate with the port on the gas warmer and/or humidifier. The multi-lumen tubing 16 can be inserted in the port to humidify a gas exiting the gas warmer, such as the carbon dioxide ($CO_2$) gas, or to add a medicament to the $CO_2$ gas exiting the gas warmer. In alternative embodiments, the multi-lumen tubing may be connected to a gas warmer only or directly to the tubing, such as a wye-tube, via a suitable air tight connector.

As shown in FIG. 9 a gas inlet port 112 is attached through a side portion of a front cap 113 of the gas humidification apparatus 100. In addition, an inlet port 115 is attached through a central portion of the front cap 113. The inlet port 115 allows for electrical components and wiring to be inserted into the gas humidification apparatus 100. The gas humidification apparatus 100 can be modified so that the ports 112 and 115 are interchanged with one another. The cap 113 may include an annular metallic heater housing (not shown) within the device housing 126 in fluid communication with the gas inlet port 112. The heater housing contains a heater cartridge that is well known in the art. When activated, the heater cartridge heats up the interior and body of the heater housing so that gases within and outside the heater housing are heated. The heater housing may include a plurality of circular holes having a diameter of approximately 0.1" (0.254 cm). Other shapes and sizes for the holes are possible, such as triangular and square shaped openings. When gas flows into the gas humidification apparatus 100 via the gas inlet port 112, the gas flows into the heater housing, where it is heated if necessary, and then flows out of the holes. The holes of the heater housing may improve the rate of heating of the gas within the gas humidification apparatus 100 and create turbulence for the gas flowing within the gas humidification apparatus 100.

The housing 126 of the gas humidifier includes a first port 116 that allows fluid to be infused by syringe, gravity feed through tubing, or by any number of pumps, to the humidification material 124. The fluids infused may include sterile water, medication, or a mixture of fluids required for merely humidification or dispensing of medication. The interior end of the port 116 is positioned so that infused fluids drip into the housing 116 and are soaked up by the entire humidification material 124 by capillary action. The housing 126 may also include a second port 118. The second port 118 is positioned between the humidification material 124 and the outlet 128 so as to allow a distal end of a catheter, such as the multi-lumen tubing 16, to be inserted into the port 118. Depending on the intended material to be delivered to the patient, the distal end of the catheter may be positioned within the port 118, within the interior of the gas humidification apparatus 100 or within a tube attached to the outlet 128 and in fluid communication with a section of a patient, or within the section of the patient. An example of a catheter that can be inserted into the gas humidification apparatus 100 is the catheter described in U.S. Pat. No. 5,964,223, previously incorporated by reference. Other devices can be inserted into the port 118 in a similar manner, such as a lumen and an endoscope. Furthermore, gases, liquids, aerosols and medicines may be conveyed to a patient by a tube or other know dispensing devices inserted through the port 118 and exiting out of the outlet 128 into the patient. Note that the materials dispensed into the port 118 by the above-mentioned dispensing devices may have properties that raise the humidity of the gas within the interior of the gas humidification apparatus 100.

Figure 9:
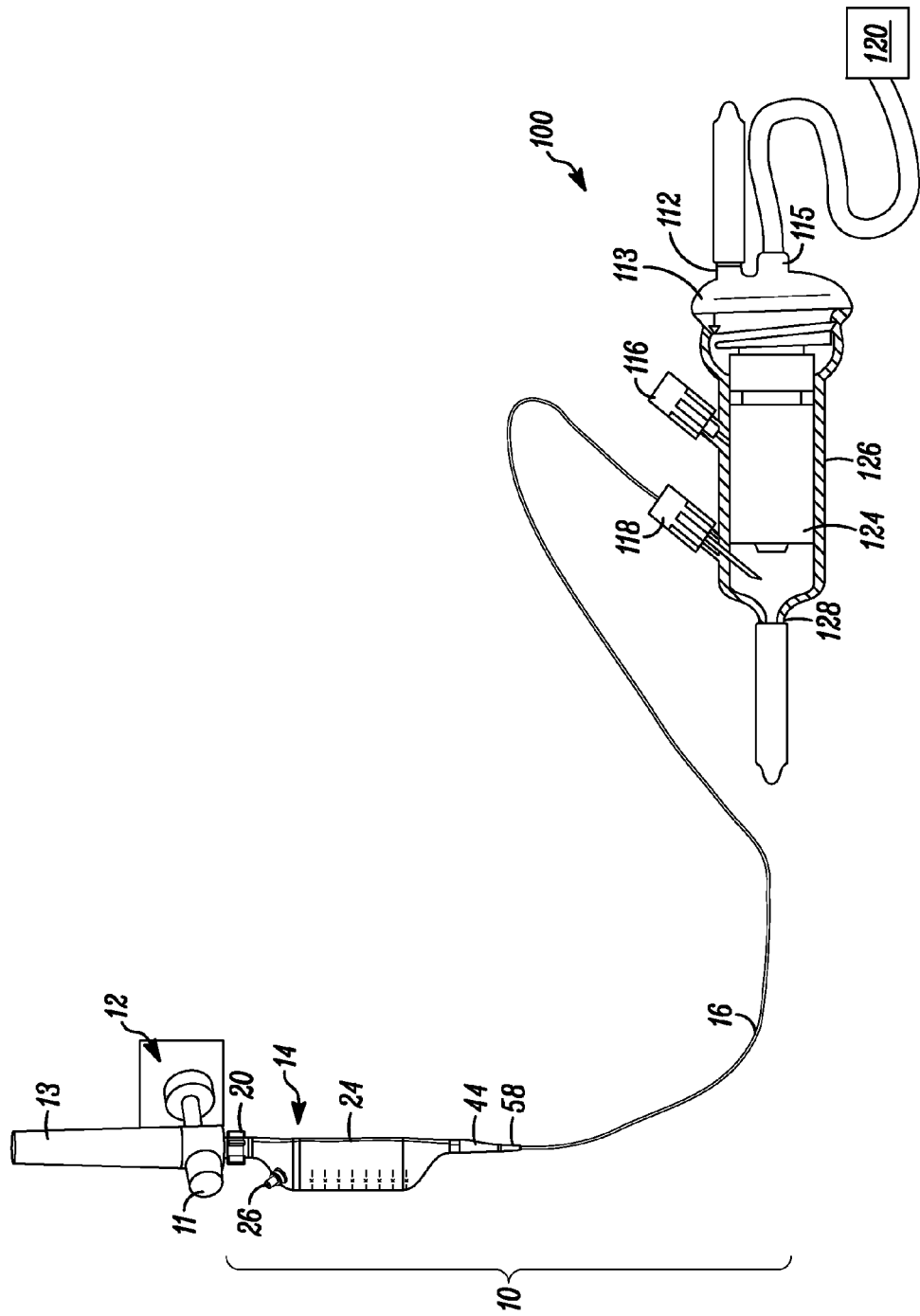
FIG. 9 illustrates an implementation of the ventilator aerosol delivery system of FIG. 1 utilizing a gas humidification and warming apparatus.

The gas humidification apparatus 100 may include control circuitry 120 that is in communication with the housing via inlet port 115. The control circuitry may include temperature sensors, humidity sensors and control circuitry so that the temperature and humidity of the gas flowing within the apparatus and delivered to a patient is controlled. In the implementation of FIG. 9, an aerosol delivery system including the liquid vessel 14, multi-lumen tubing 16 and gas humidifier 100 may be used for endoscopic procedures, such as a laparoscopic procedure. Other configurations are also contemplated.

An aerosol delivery system 10 has been described that, in one implementation, may be a single-use (disposable) continuous nebulizer system designed for use with mechanically ventilated patients to aerosolize physician-prescribed medications for inhalation which are approved for use with a general purpose nebulizer. The system 10 separates the liquid reservoir from the nebulization process taking place at the adapter hub where it fits into an endotracheal tube (ETT) by a long (for example 3 meter) multi-lumen tube 16 comprising multiple outer lumens 52 supplying air with the central lumen 50 containing the liquid to be nebulized as the result of the Venturi effect at its distal end where it comes into contact with the air supply. The liquid reservoir 34 can therefore be mounted away from the immediate treatment zone, avoiding concerns about the effect of orientation that are associated with other types of nebulizers having a self-contained reservoir. The system can produce aerosols having a wide range of droplet sizes, depending upon central lumen diameter, with values of MMAD that range from 4 to 30 μm. In another implementation, the aerosol delivery device may be configured for non-respiratory applications, such as endoscopic procedures including laparoscopy, for example by inserting the distal end of the multi-lumen tubing into an inlet port of a tubing, a gas warmer, a gas warmer/humidifier or other device suitable for use in an endoscopic procedure, rather than into an endotracheal tube adapter.

It is therefore intended that the foregoing detailed description be regarded as illustrative rather than limiting, and that it be understood that it is the following claims, including all equivalents, that are intended to define the scope of this invention.

We claim:

1. An aerosol delivery system comprising:
   a vessel comprising:
      a first end comprising a resealable fitting for connecting with a gas supply;
      a body having a liquid reservoir and a gas passage independent of the liquid reservoir, wherein the liquid reservoir and the gas passage are in communication with the gas supply via the resealable fitting, and wherein the body is configured to be adjacent to the resealable fitting when the resealable fitting is attached to the gas supply; and
      a second end connected with a length of multi-lumen tubing, the second end defining a liquid path from the liquid reservoir and to a liquid lumen in the multi-lumen tubing, and a gas path from the gas passage to at least one gas lumen in the multi-lumen tubing;
   a tube adapter having an inlet port connected to an end of the multi-lumen tubing, a tube opening sized to connect with a tube, wherein outlets for the gas and liquid lumens at the end of the multi-lumen tubing are arranged such that a gas issuing from the at least one gas lumen and liquid issuing from the liquid lumen continuously form an aerosol inside the tube adapter; and
   wherein the first end of the vessel further defines a channel configured to direct a first portion of the gas received at the resealable fitting into the gas passage and a second portion of the gas to the liquid reservoir.

2. The aerosol delivery system of claim 1, wherein the body further comprises a one-way filling port positioned over the liquid reservoir of the vessel, the one-way filling port positioned to permit refilling of the liquid reservoir.

3. The aerosol delivery system of claim 2, wherein the one-way filling port is positioned at an angle from a vertical orientation of the body.

4. The aerosol delivery system of claim 3, wherein the vessel and the tube adapter are separated by at least 3 feet by the multi-lumen tubing.

5. The aerosol delivery system of claim 4, wherein the resealable fitting on the vessel is configured to rigidly attach the vessel to an outlet of the gas supply, when the resealable fitting is tightened onto the outlet.

6. The aerosol delivery system of claim 4, wherein the multi-lumen tubing is at least 8 feet long.

7. The aerosol delivery system of claim 5, wherein the continuously formed aerosol produced in the tube adapter comprises particle sizes in a range of 10-14 μm MMAD when gas at a pressure of 50 pounds per square inch (psi) is received at the resealable fitting.

8. The aerosol delivery system of claim 1, wherein the liquid comprises one or more of salbutemol, budesonide and ipratropium.

9. The aerosol delivery system of claim 1, wherein the body is configured to be vertically aligned by the resealable fitting when the resealable fitting is attached to the gas supply.

10. The aerosol delivery system of claim 1, wherein the tube opening of the tube adapter is sized to connect with an endotracheal tube.

11. The aerosol delivery system of claim 10, wherein the tube adapter further comprises a suction catheter opening sized to connect with a suction catheter.

12. The aerosol delivery system of claim 1, wherein the tube adapter comprises an endotracheal tube adapter.

13. The aerosol delivery system of claim 1, wherein the tube adapter comprises a wye-tube.

14. An aerosol delivery system comprising:
a vessel comprising:
- a first end comprising a resealable fitting for connecting with a gas supply;
- a body having a liquid reservoir and a gas passage independent of the liquid reservoir, wherein the liquid reservoir and the gas passage are each in direct communication with gas supply via separate channels positioned in the first end adjacent to the resealable fitting, and wherein the body is configured to be adjacent to the resealable fitting when the resealable fitting is attached to the gas supply; and
- a second end connected with a length of multi-lumen tubing, the second end defining a liquid path from the liquid reservoir to a liquid lumen in the multi-lumen tubing, and a gas path from the gas passage to at least one gas lumen in the multi-lumen tubing; and
- an inlet port resealably connected to an end of the multi-lumen tubing, wherein outlets for the gas and liquid lumens at the end of the multi-lumen tubing are arranged to continuously form an aerosol at the inlet port when a gas issues from the at least one gas lumen and a liquid issues from the liquid lumen.

15. The aerosol delivery system of claim 14, wherein the gas is configured for use in an endoscopic procedure.

16. The aerosol delivery system of claim 14 wherein, at the second end of the vessel, an end the multi-lumen tubing is connected to a bottom portion of the reservoir and positioned to receive the liquid from the liquid reservoir and a side of the multi-lumen tubing is formed with an opening in each of the at least one gas lumens and positioned to receive the gas from the gas passage.

* * * * *